United States Patent
Sabsabi et al.

(10) Patent No.: US 10,024,802 B2
(45) Date of Patent: Jul. 17, 2018

(54) METHOD FOR LASER-INDUCED BREAKDOWN SPECTROSCOPY AND CALIBRATION

(71) Applicant: NATIONAL RESEARCH COUNCIL OF CANADA, Ottawa (CA)

(72) Inventors: Mohamad Sabsabi, Longueuil (CA); Jean-Pierre Monchalin, Montréal (CA); René Héon, Boucherville (CA); Paul Bouchard, Montréal (CA)

(73) Assignee: National Research Council of Canada, Ottawa, Ontario (CA)

( * ) Notice: Subject to any disclaimer, the term of this patent is extended or adjusted under 35 U.S.C. 154(b) by 0 days.

(21) Appl. No.: 15/320,499

(22) PCT Filed: Jun. 19, 2015

(86) PCT No.: PCT/IB2015/054628
§ 371 (c)(1),
(2) Date: Mar. 8, 2017

(87) PCT Pub. No.: WO2015/193850
PCT Pub. Date: Dec. 23, 2015

(65) Prior Publication Data
US 2017/0191940 A1 Jul. 6, 2017

Related U.S. Application Data

(60) Provisional application No. 62/014,944, filed on Jun. 20, 2014.

(51) Int. Cl.
*G01J 3/30* (2006.01)
*G01N 21/71* (2006.01)
(Continued)

(52) U.S. Cl.
CPC ......... *G01N 21/718* (2013.01); *G01N 21/274* (2013.01); *G01J 3/02* (2013.01); *G01J 3/44* (2013.01); *G01N 21/64* (2013.01)

(58) Field of Classification Search
CPC .. G01N 21/718; G01N 21/274; G01N 21/645; G01N 21/6458; G01J 3/44; G01J 3/4406; G01J 3/02
See application file for complete search history.

(56) References Cited

U.S. PATENT DOCUMENTS

| | | |
|---|---|---|
| 4,986,658 A | 1/1991 | Kim |
| 2002/0149768 A1 | 10/2002 | Sabsabi et al. |
| 2012/0099103 A1* | 4/2012 | Hahn ............... G01N 21/718 356/316 |

FOREIGN PATENT DOCUMENTS

| | | |
|---|---|---|
| CA | 2014366 | 10/1990 |
| EP | 0392337 | 2/1994 |

OTHER PUBLICATIONS

N.B. Zorov, A.A. Gorbatenko, T.A. Laburtin, A.M. Popove, "A review of normalisation techniques in analytical atomic spectrometry with laser sampling: from single to multivariate correction", Spectrochimica Acta, 2010, Part B. vol. 65, pp. 642-657.

(Continued)

*Primary Examiner* — Abdullahi Nur
(74) *Attorney, Agent, or Firm* — Catherine Lemay

(57) ABSTRACT

A method for laser induced breakdown spectroscopy (LIBS) calibration or LIBS assay comprises providing a plurality of reference samples, each having a respective, known concentration of an analyte, assaying each reference sample to obtain a respective LIBS spectrum, and for each reference LIBS spectrum, measuring an intensity of at least one spectral analyte line that varies with concentration of the analyte, and measuring a peak amplitude of at least one (Continued)

saturating line of a reference element. The ratio and known concentrations define a calibration curve for the analyte.

11 Claims, 7 Drawing Sheets

(51) Int. Cl.
*G01N 21/27* (2006.01)
*G01J 3/02* (2006.01)
*G01N 21/64* (2006.01)
*G01J 3/44* (2006.01)

(56) References Cited

OTHER PUBLICATIONS

C.B. Stipe, B.D. Hensley, J.L. Boersema and S.G. Buckley, Laser-Induced Breakdown Spectroscopy of Steel: A comparison of Univariate and Multivariate Calibration Methods, Applied Spectroscopy, 2010, vol. 65, pp. 154-160.
International Search Report and Written Opinion, dated Sep. 3, 2015.
International Preliminary Report on Patentability, dated Dec. 20, 2016.

* cited by examiner

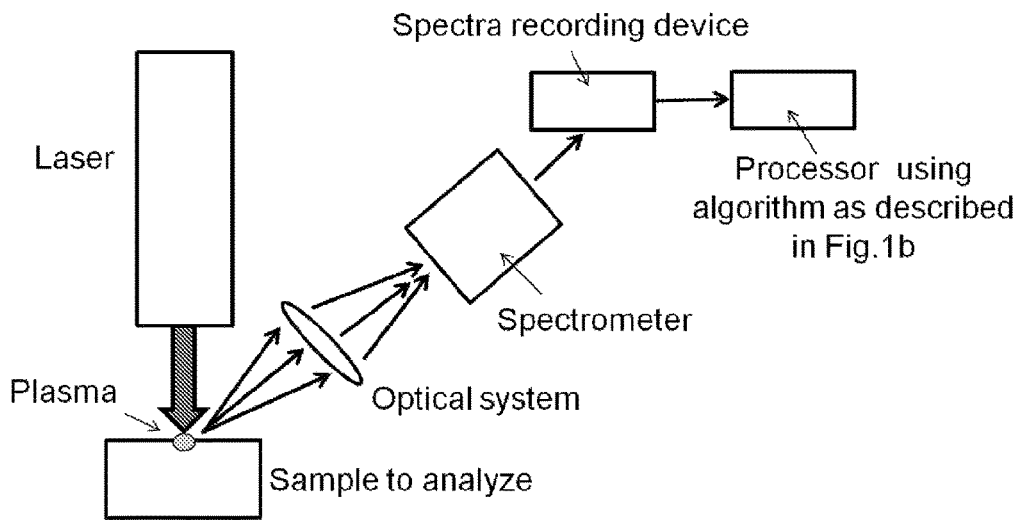
Fig. 1a: previous art
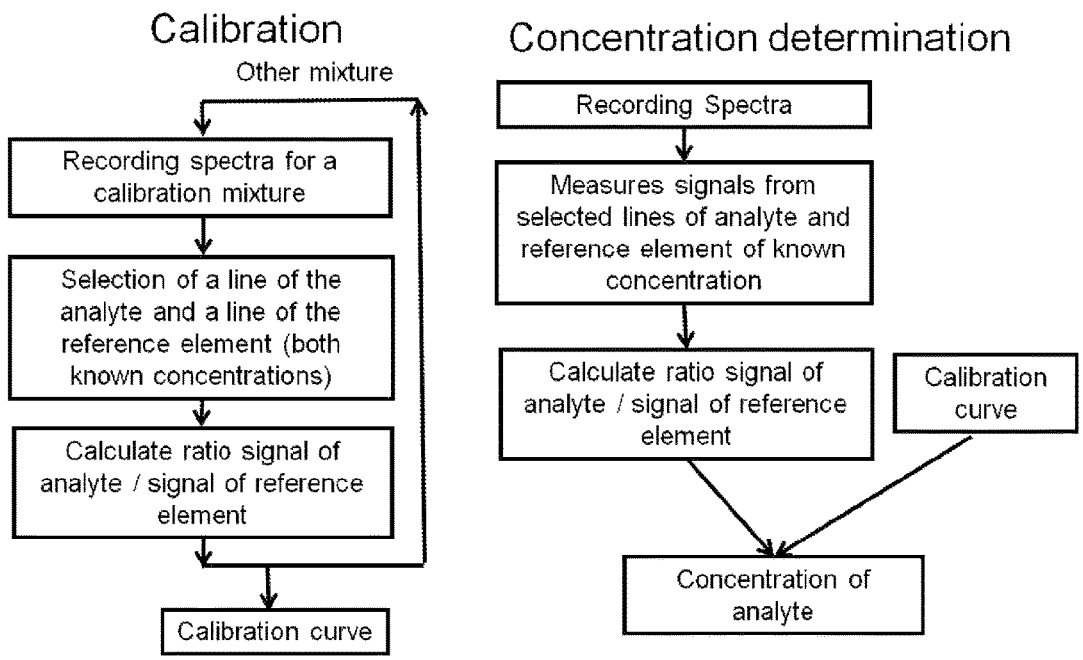
Fig. 1b: previous art

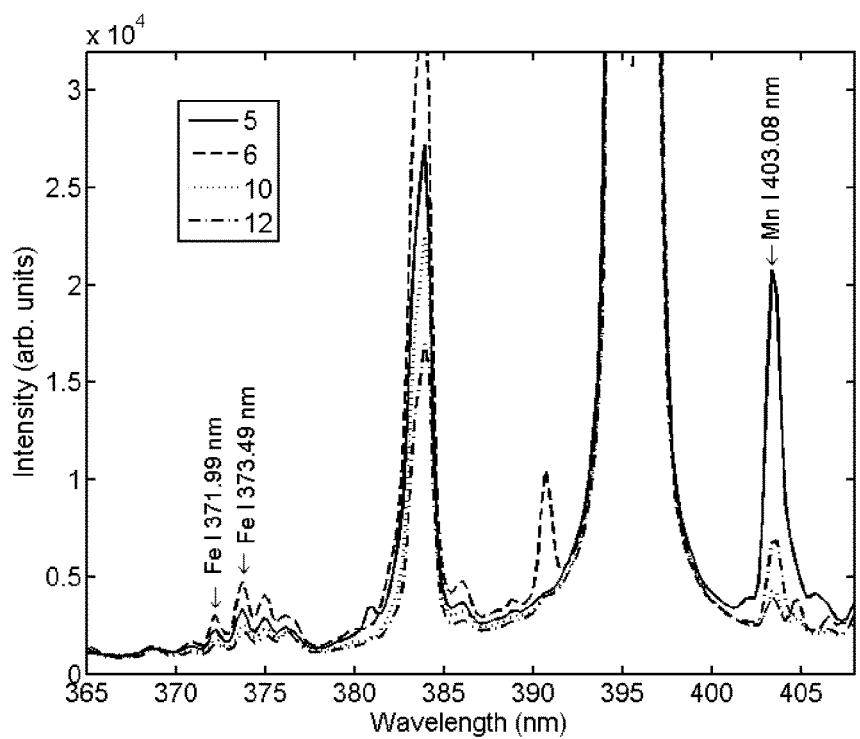
Fig. 2
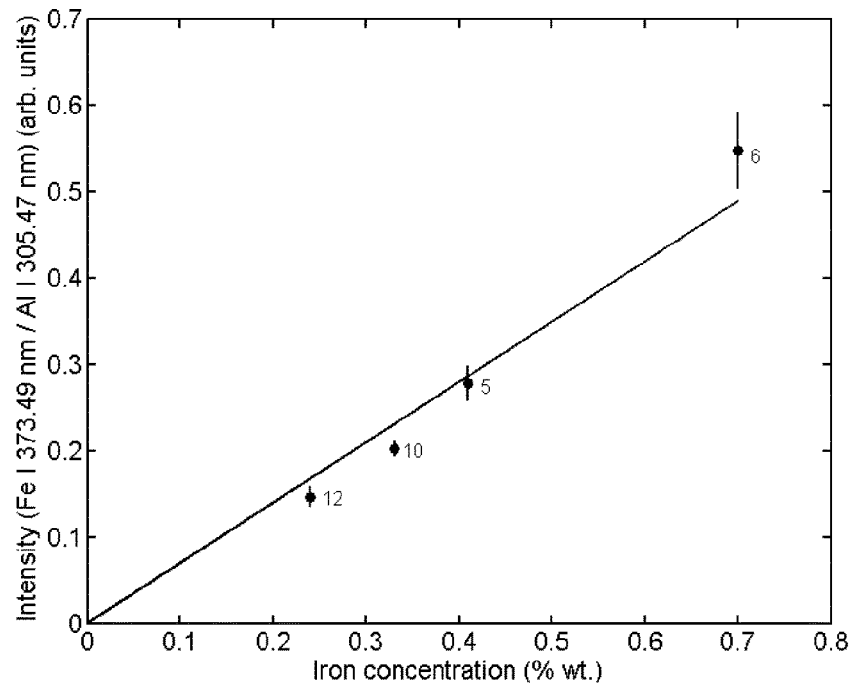
Fig. 3: according to previous art

US 10,024,802 B2

METHOD FOR LASER-INDUCED BREAKDOWN SPECTROSCOPY AND CALIBRATION

CROSS-REFERENCE TO RELATED APPLICATIONS

This application is a national stage entry of International Patent Application PCT/IB2015/054628 filed Jun. 19, 2015 and claims the benefit of U.S. Provisional Patent Application Ser. No. 62/014,944 filed Jun. 20, 2014.

FIELD OF THE INVENTION

The present invention relates in general to performing and calibrating laser-induced breakdown spectroscopy (LIBS) systems and, in particular, to doing so when no major component of the sample is known beforehand.

BACKGROUND OF THE INVENTION

Laser induced breakdown spectroscopy (LIBS) is a well-known analytical technique that involves producing a plasma at a surface of a material and analyzing a spectrum of emitted light from the plasma. LIBS provides rapid, in situ, compositional analysis without touching the surface. LIBS is now employed in a wide range of applications such as, the monitoring of active agents in pharmaceutical pills, the detection at a distance of explosives, the determination of the composition of molten metallic alloys and the determination of materials used in ancient paintings and sculptures.

FIG. 1a is a schematic illustration of a typical embodiment of a LIBS system known in the art. The LIBS system includes a short pulse laser, such as Q-switched Nd-YAG laser, that produces plasma at the surface or within the sample (which may be a solid, liquid or gas, or even a complex mixture of any of those such as a slurry). During LIBS, chemical bonds are essentially broken and the material is dissociated into its elemental constituents that are excited to higher level energy states and emit light while losing their excitation energy into lower levels. As each element has its own energy state structure, the wavelengths of the emitted light are used as an index of the elements present in the plasma. Light from the plasma is then collected by a spectrometer, with attendant optical collection system. The intensity of the spectral lines is associated with quantitative information of the elements present in the material.

A typical spectrometer has a light dispersing element, such as a diffractive grating, and the spectrum is recorded by a spectra recording device, such as an array of photomultipliers at defined locations along the dispersed spectrum, or by a camera. The data is then received by a processor.

As with any metrological system, a LIBS system has to be calibrated. This is usually performed with a set of samples of known composition. Since the actually recorded signal depends on many variables such as laser power, ablated mass, atomized mass, plasma temperature, plasma expansion, collected light efficiency, spectrometer dispersing specifications, detector sensitivity, sample characteristics, etc., each recorded spectral signal has to be normalized in order to derive a reproducible measurement.

There are several ways to perform this normalization as explained in the review publication "*A review of normalisation techniques in analytical atomic spectrometry with laser sampling: from single to multivariate correction*" by N. B. Zorov, A. A. Gorbatenko, T. A. Laburtin, A. M. Popov published in Spectrochimica Acta Part B, vol. 65, pp. 642-657 (2010), but the most widely applied is based on an internal standard. This involves taking a ratio of the line intensity of the analyte (element whose concentration has to be determined) to the one of a reference element (the internal standard) which is present in the analyzed material and in the plasma.

This procedure is shown in FIG. 1b (left side). A spectrum is recorded for a calibration mixture, which has known elemental composition, at least in respect of a reference element and the analyte. An identifying spectral line of the analyte and one of the reference element are then selected. Both lines should be well separated from each other, and from adjacent spectral lines of other expected elements in the sample and calibration mixture, to avoid interference from neighboring emission lines of other elements. Line intensity of the analyte should be proportional to its concentration. Attributes of these lines, either their peak amplitudes or their integrated intensities through the resolving bandwidth of the spectrometer, are then measured and their ratios calculated. By performing measurements on one or more calibration mixtures (internal standards) and of the reference element, a calibration curve may be produced that relates the calculated ratio to the concentration of the analyte. From this calibration curve, knowing the concentration of the reference element, the concentration of the analyte can then be determined.

The right hand side of FIG. 1b shows LIBS assaying according to prior knowledge. The recorded spectrum is received from the LIBS apparatus. Signals from the selected lines of the analyte and reference element, the latter of which having a known concentration in the sample, are measured. A ratio of the signal of the analyte to the signal of the reference element is computed. The calibration curve is used to return a concentration of the analyte.

An implementation of this procedure is illustrated with the example of an aluminum alloy, the reference element being aluminum and the analyte iron. Typically in aluminum alloys, aluminum has a concentration that ranges from 90 to 100%, so a variation of the concentration of a minor element (which is the analyte) does not change significantly the concentration of the reference element. FIG. 2 shows a part of the spectrum between 365 and 407.5 nm of an acquisition spectral window recorded between 250 and 420 nm for 4 samples labeled 5, 6, 10 and 12 and including the 373.49 nm line of neutral iron (Fe I) used for iron concentration determination. The 305.47 nm line of aluminum that is used for the reference element is outside of the shown part in FIG. 2.

FIG. 3 shows a calibration straight line that relates intensity ratio to iron concentration. Such a calibration curve can be used as described above to determine a concentration of iron in an aluminum sample by the LIBS technique.

Unfortunately, this procedure requires a known concentration of a reference element in the sample, and a calibration curve (based on internal standards), to generate the calibration curve. It is often desired to determine composition of complex mixtures of materials in which there is no single major element known beforehand.

It is an object of this invention to provide a method that allows for the determination of the concentration of an analyte in a material for which a major component of the material is not initially known. This method may be implemented in a processor coupled to a LIBS system.

As prior art, the EP 0392337 to Carlhoff et al. describes a method for determining the concentration ratio of two elements (a and b) of an unknown substance from the intensity ratio of two spectral lines of these elements in a plasma of this substance. In accordance with their method, in addition to the intensity ratio, the intensity ratio of two spectral lines 1 and 2 of a third element (c, which may be the same as one of a or b), present in the substance, at different excitation energies E1 and E2 is determined and then the concentration ratio of a to b is determined according to conventional calibration using comparable samples.

SUMMARY OF THE INVENTION

Applicant has devised a method for LIBS quantification based on finding, within the sample under test, at least one element having at least one line that is saturating. This element serves as the reference element, and its line, the internal standard.

This element is a minor element of unknown concentration within the mixture, otherwise, if it is a major element with known concentration, the previous art procedure can be applied. To serve as the internal standard, the reference element has to be in sufficient concentration, and the line sufficiently strong, to saturate the line, but this does not require that the element constitute a major component of the sample under test.

Applicant has discovered that if one uses a spectrometer with capability of resolving line shape and tuned to line center, it is then possible to get the desired internal standard. As shown from the formula giving I(v), at line center $v_0$, when the concentration is sufficient and the line sufficiently strong, $I(v_0)$ saturates and becomes independent of the concentration and this occurs independently of the line shape: $I(v_0)=Kp$.

Accordingly, there is also provided a laser induced breakdown spectroscopy (LIBS) method, comprising: providing one or more reference samples, each having a respective, known concentration of an analyte; assaying each reference sample to obtain a respective LIBS spectrum; for each reference LIBS spectrum, measuring an intensity of at least one spectral analyte line that varies with concentration of the analyte, and measuring a peak amplitude of at least one saturating line of a reference element; and computing a ratio of the intensity to the amplitude as a function of the known concentration of the analyte, to produce a calibration curve for the analyte.

In one aspect, the samples may be complex mixtures. For example, the materials can be solid, liquid, gas or a mixture thereof. In one aspect, the complex mixture is a composed of a mixture of solid/liquid (e.g. slurries), solid/gas (e.g. aerosols, dust in air, ashes), liquid/gas (e.g. bubbles), liquid/ liquid (e.g. oil, water, bitumen). In one aspect, the samples are slurries, aerosols, emulsions, or bubbles.

The peak amplitude may be measured by an integrated intensity within a spectral band narrower than ½ a bandwidth of the saturating line that includes the peak of the saturating line. The amplitude of the saturated line may also be measured by a signal from a single narrow bandpass optical filter associated with a spectral feature of the line.

In yet another aspect, computing the ratio as a function of the concentration comprises performing a linear regression.

In another aspect, two or more saturating lines or two or more analyte lines are measured concurrently to improve calibration accuracy.

Providing the reference samples may comprise applying chemometric methods to measure the concentrations in the reference samples.

In a further aspect, the one or more of the at least one saturating line is used for normalizing intensities of at least one analyte line for each of a plurality of analytes.

In yet a further aspect, the method further comprises the following:

providing a test sample;
assaying the test sample to obtain a test LIBS spectrum;
measuring a test intensity of the test LIBS spectrum at one or more of the at least one spectral analyte line;
measuring a test peak amplitude of the test LIBS spectrum at one or more of the at least one saturating line; and
interpolating a concentration of the analyte in the test sample from a ratio of the test intensity to the test peak amplitude.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 1a is a block diagrams showing prior art calibration and LIBS assay methods;

FIG. 1b is a schematic illustration of a prior art LIBS apparatus;

FIG. 2 is a plot of acquired spectra of 4 samples using the method and apparatus of FIG. 1;

FIG. 3 is a calibration curve derived from the spectra of FIG. 2;

DESCRIPTION OF PREFERRED EMBODIMENTS

Figure 4A:
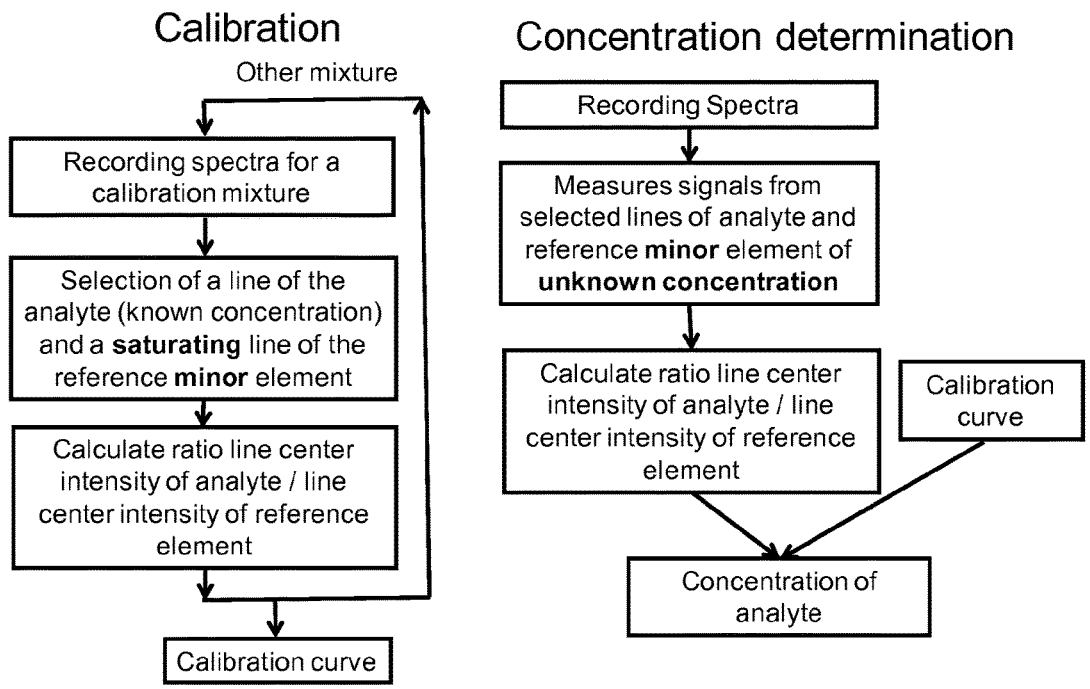
FIG. 4a a block diagrams showing calibration and LIBS assay methods in accordance with an embodiment of the present invention.

Herein, the following notations are used:
$m_{abl}$: ablated mass per unit surface;
$f_a$: fraction of the ablated mass that is atomized;
$m_{at}$: atomic mass of the tracked element (either the analyte or the reference element);
C: atomic concentration (of the analyte or the reference element) in the mixture;

$n_o$: atomic density in the plasma (of the analyte or of the reference element) assumed to be approximately uniform throughout the plasma plume;
d: thickness of the plasma in the direction of the line of collection of plasma light;
S: apparent surface of the plasma;
$C_{sp}$: is a collection efficiency factor depending upon the collection optics and upon the spectrometer;
$h\nu_0$: photon energy at the line center $v_0$;
$g_1$ is the degeneracy of the lower energy level;
$g_2$: degeneracy of the upper energy level;
A: Einstein coefficient of spontaneous emission;
k: Boltzmann constant;
c the speed of light;
T: absolute temperature;
U(T) : partition function at temperature T; and
$g(v-v_0)$: line shape function which is normalized (i.e. the positive semi-infinite integral of $g(v-v_0)$ dv=1).

The number of atoms in the plasma is then: $n_o$ d S=$M_{abl}$ $f_a$ (C/$m_{at}$). Following textbooks such as Spectrophysics: Principles and Applications by A. Thorne, U. Litzen and S. Johansson, Springer, 1999, the intensity I(v) collected by the spectrometer at the light frequency v is then (neglecting absorption) (eq1):

$$I(v)=C_{sp} h v_0 g_2 A (e^{(-h\,v_0/kT)}/U(T))\, g(v-v_0)\, S\, d\, n_o.$$

In general Stark broadening dominates, so $g(v-v_0)$ is a Lorentzian function (eq2):

$$g(v-v_0)=\{\pi\Delta v[1+(v-v_0/\Delta v)^2]\}^{-1}$$

where $2\Delta v$ is the full linewidth at half maximum. However in practice absorption cannot be neglected, and in the eq1, d $n_o$ has to be replaced by the integral from 0 to d of $n_o e^{-a(z)z}$dz, where the absorption coefficient a(z) is given by (eq3):

$$a(z)=n_o\, (g_2/g_1)\, (c^2/8\pi v_0^2)\, A\, g(v-v_0),$$

After integration through the plasma plume from 0 to d we find (eq4):

$$I(v)=K_p\,[1-e^{-KCg(v-v_0)}],$$

in which the constants K and $K_p$ are (eq5):

$$K=(g_2/g_1)\, (c^2/8\pi v_0^2)\, A\, m_{abl}f_a/m_{at}, \text{ and}$$

$$K_p=C_{sp} h\, v_0\, g_1\, (8\pi v_0^2/c^2)\, S\, (e^{(-h\,v_0/kT)}/U(T)). \quad\quad (eq6)$$

If the equation above is integrated over the emission line using a spectrometer with poor resolving power, one obtains what is known as the curve-of-growth: see Chapter 9 in the textbook *Spectrophysics: Principles and Applications* mentioned above. The result is always dependent upon the concentration C of the element: at lower concentration the variation is linear and at higher concentration, it is slower and tends to vary as the square root of concentration. Anyhow, since the curve-of-growth depends upon concentration, it is not possible to use it as an internal standard when the concentration of the element is unknown.

Applicant has found that if one uses a spectrometer with capability of resolving line shape and tuned to line center, it is then possible to obtain an internal standard. As shown from eq4, at a line center $v_0$, when the concentration is sufficient, and the line is sufficiently strong, $I(v_0)$ saturates and becomes independent of the concentration. Saturation occurs independently of the line shape: $I(v_0)=K_p$.

FIG. 4a, left side, is a schematic flowchart showing principal steps involved in an embodiment of the present invention. A spectrum is recorded for a calibration mixture. The calibration mixture has a known concentration of the analyte, but it is not known what elements are present in minor amounts. The line of the analyte is selected and a saturated line is identified to serve as the reference. The signal that is measured is the intensity at line center or at least the integrated intensity within a spectral band much narrower than the width of the line (which is why a spectrometer capable of resolving line shape is used). By taking the ratio of the signal of the analyte (of known concentration) and the signal from a saturating line of the reference, a calibration curve can be built.

As is well known in the art, saturation of a line depends on the emission strength of the line once a threshold concentration of the element is present. Some spectral lines are present with much greater amplitude than others. The saturated lines are typically not useful for calibration or quantification, they exhibit no observed difference in signal strength as a function of concentration (beyond the threshold). Whether a line is saturated or not, can be determined, for example, by comparing spectra of different quantities of the analyte of interest with each other, where each of the spectra has the threshold concentration of the element or more. The line saturation is related to the intrinsic physical properties (described, for instance, by the Einstein coefficient) of the atomic structure where the transition between an upper and lower energy level occurs. This is the primary factor involved in the saturation effect. The second factor is the threshold concentration value of the reference element.

Figure 4B:
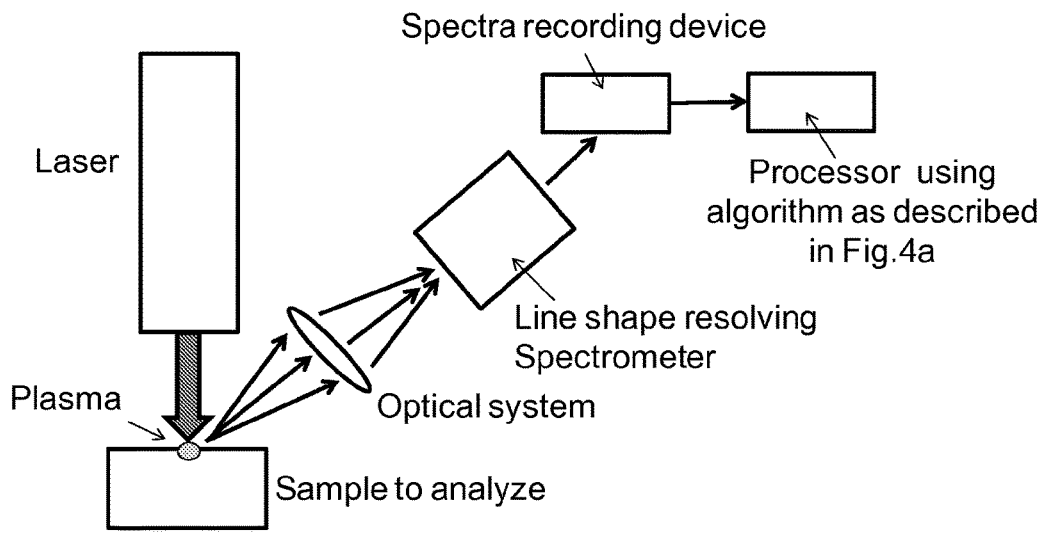
FIG. 4b is a schematic illustration of a LIBS apparatus in accordance with an embodiment of the present invention.

FIG. 4b is a schematic illustrations of a system for LIBS assaying, different from the prior art in that the spectrometer has a resolution necessary for resolving a line shape of the saturated line (which is not a general requirement for LIBS), and that the processor is programmed to apply a method of FIG. 4a. The other elements of the system are substantially standard LIBS elements such as a pulsed laser, focusing optics (not represented in the figure) and collecting optics. The processor which processes the algorithm described in FIG. 4a is typically a computer, having a non-volatile memory.

It should also be noted that instead of using a grating-based, or diffraction-based spectrometer a set of light filters can be used. Depending upon the required resolution, these filters can be interference filters, Fabry-Perot etalons or Lyot filters. A practical system can be for example one that includes a relatively coarse resolution spectrometer with high throughput (broad slit opening) combined with a high resolution filter specifically tuned to the center of the saturating line of the internal standard, because the saturating line requires a substantially higher resolution than the analyte line.

Once calibration has been performed, and a calibration curve is generated, concentration of the analyte can be measured from the ratio of intensities at line center and the calibration curve (see FIG. 4a, right side).

EXAMPLES

This invention has been successfully applied with the same aluminum alloy example used to illustrate previous art (FIGS. 2 and 3). Data was obtained with a system first composed of a pulsed Q-switched Nd:YAG laser operating at 1064 nm with a pulse duration between 5 to 10 ns and delivering about 200 mJ energy per pulse. Focusing was performed with a first plano-convex lens of 25-cm focal length, giving a circular spot on the surface between 0.5 and 1 mm diameter. Ablation was performed in air at atmospheric pressure and the repetition rate was 3 Hz, to prevent any interaction between the laser and aerosols. An exhaust removal and blower fan was also positioned next to the plasma to limit any interaction between the laser and aerosols, and improve the shot-to-shot reproducibility.

The light emitted by the plasma was collected by a second plano-convex lens (25.4-mm diameter, 20-cm focal length) onto the entrance slit 50 μm wide of a Czerny-Turner spectrometer. The second plano-convex lens had a focal length of 67 cm, and a f-number of 5.8. The spectrometer was equipped with a 150 lines/mm (blazed at 500 nm) grating. The spectrometer was coupled to an intensified CCD camera containing 1024×256 pixels of 25×25 μm$^2$ dimension, for recording the spectrum. The acquisition window ranged from 250 to 420 nm and the spectral resolution was about 0.17 nm. This spectral resolution was sufficient to capture essentially the center of emission lines according to the invention. Finally, to achieve the optimum experimental conditions, the acquisition delay was set to t=5 μs while the gate width was fixed to M=4 μs.

Reference samples were provided, having the properties shown in Table 1:

| Sample designation | Concentration (wt. %) | | |
| --- | --- | --- | --- |
| | Mg | Fe | Al |
| 5 | 1.15 | 0.41 | 96.817 |
| 6 | 1.56 | 0.70 | 87.541 |
| 10 | 1.07 | 0.33 | 97.047 |
| 12 | 0.77 | 0.24 | 97.124 |

Figure 5:
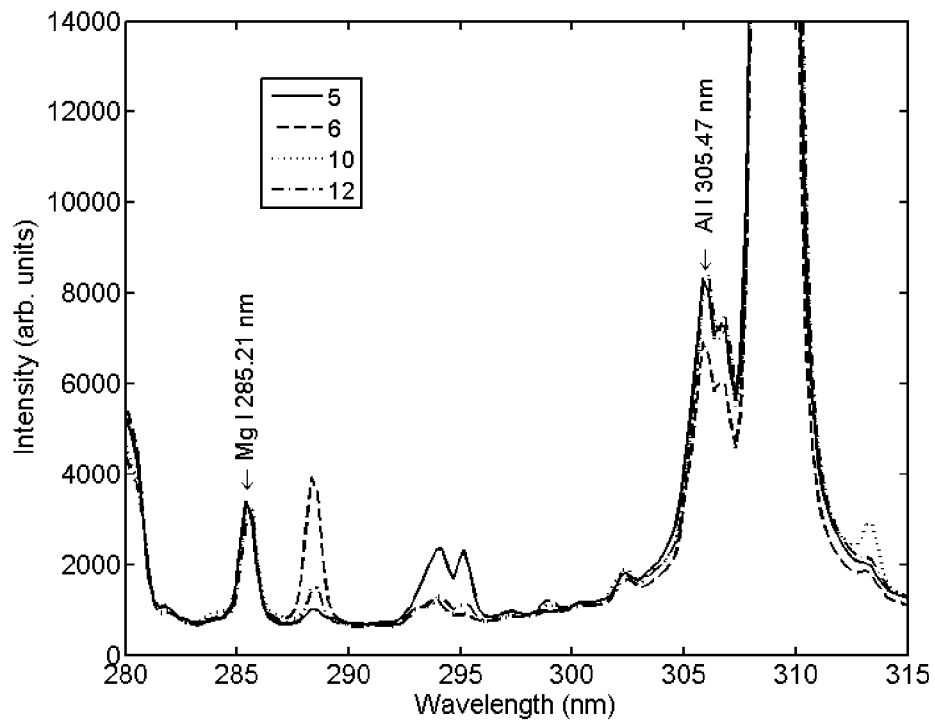
FIG. 5 is a plot of acquired spectra of 4 samples using the method and apparatus of FIG. 4.
Figure 6:
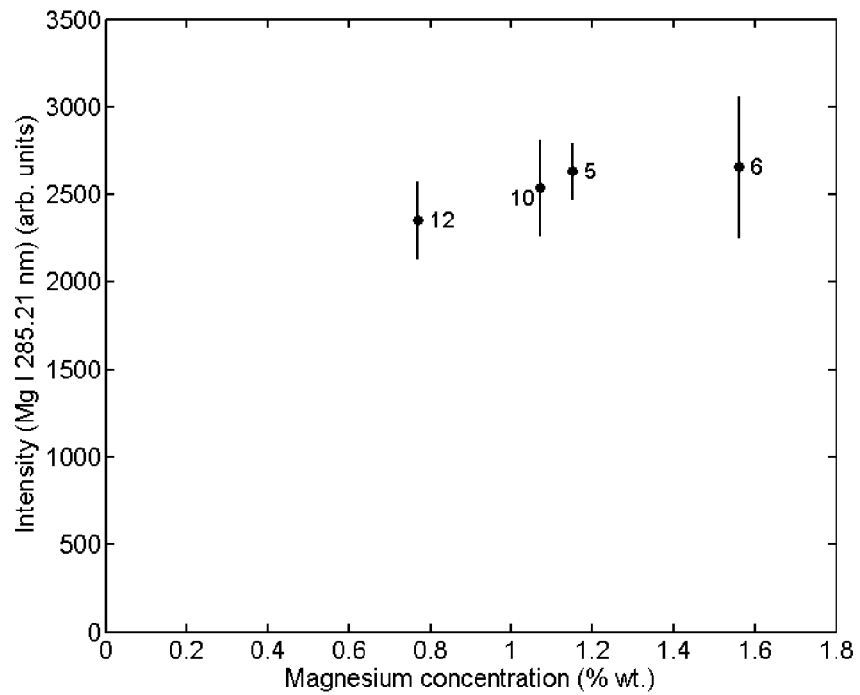
FIG. 6 shows in finer detail, the saturation of the spectrum at the Mg I line.

FIG. 5 plots spectra samples 5, 6, 10, and 12. As will be noted, peaks near 280 nm, near 288.5 nm, and near 313 nm all show variation as a function of concentration of Al, but the Mg I line at 285.21 nm is saturating, showing a same amplitude for each concentration. FIG. 6 plots intensity (arbitrary units) at 285.21 nm as a function of a determined Mg concentration. The error bars show that the curve is substantially flat within the uncertainty of measure.

Figure 7:
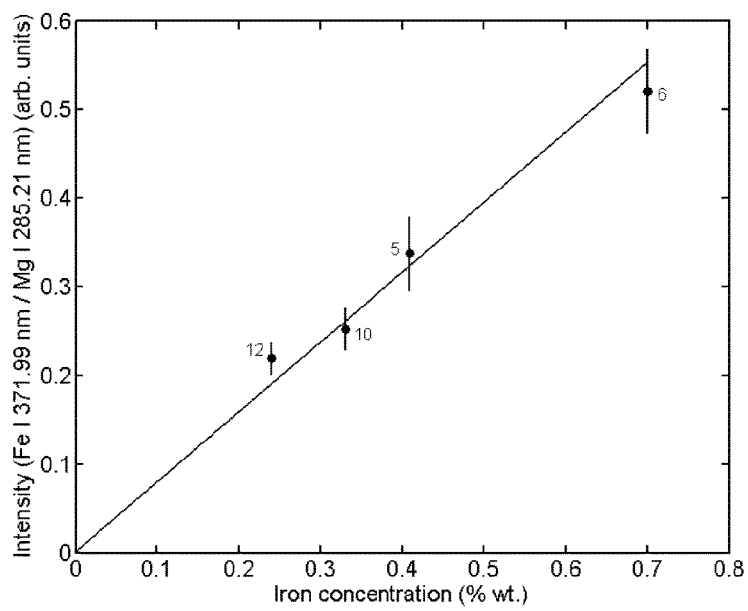
FIG. 7 is a calibration curve derived from the spectra of FIG. 5 in accordance with an embodiment of the present invention.

FIG. 7 shows the calibration curve that plots the ratio of the Fe I 371.99 nm line to the saturating Mg I 285.21 nm line according to an example of the invention. This simple example of LIBS assaying of aluminum alloys, demonstrated an excellent calibration curve, which happens to be better than that of FIG. 3. One reason for this is that uncertainties with respect to concentrations of two variables need to be ascertained according the method of FIG. 1a, while the method of FIG. 1b is dependent only on a sufficient concentration of the element having the saturation line, which decreases the experimental error. This novel calibration approach is an alternative to the standard calibration based technique, and can be applied in situations where quantification of the reference element is not independently performed (or otherwise available).

It will be noted that the saturating line of the internal standard was recorded with the same high resolution spectrometer as for the analyte line, however, given the difference in the required resolution, it may be more convenient in other applications to use a coarser resolution for the analyte line measurements (e.g. one that provides integration over the line shape) than is used for the saturating line, which records only the line center of the saturating line.

As mentioned above, this invention is particularly useful for complex mixtures in which there is no element with known concentration to be used as internal reference. This occurs in particular in slurries of mineral ores. A nickel slurry is LIBS assayed to evaluate a concentration of magnesium, for downstream pyro-metallurgy processing. This slurry contains also iron in appreciable quantity for which line saturation occurs.

Figure 8:
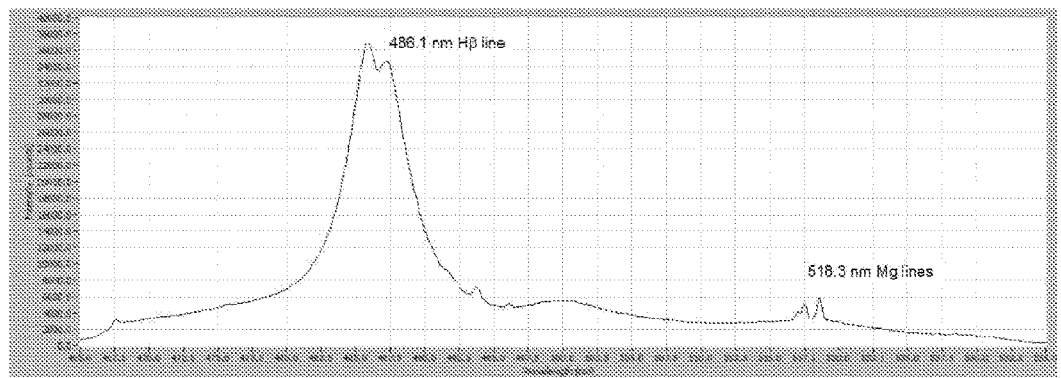
FIG. 8 shows a spectrum obtained on a nickel ore slurry jet showing the Hβ hydrogen line at 486.1 nm and the magnesium triplet lines around 518.3 nm.

FIG. 8 shows part of the spectrum collected on such slurry. The spectrum was obtained from an approximately 1 mm diameter spot at the surface of a slurry jet containing 2.5% of Mg by firing a single laser pulse shot of 180 mJ energy provided by a Nd:YAG laser, at a wavelength of 1064 nm. An acquisition delay of 1 μs and integration time of 5 μs were used.

Figure 9:
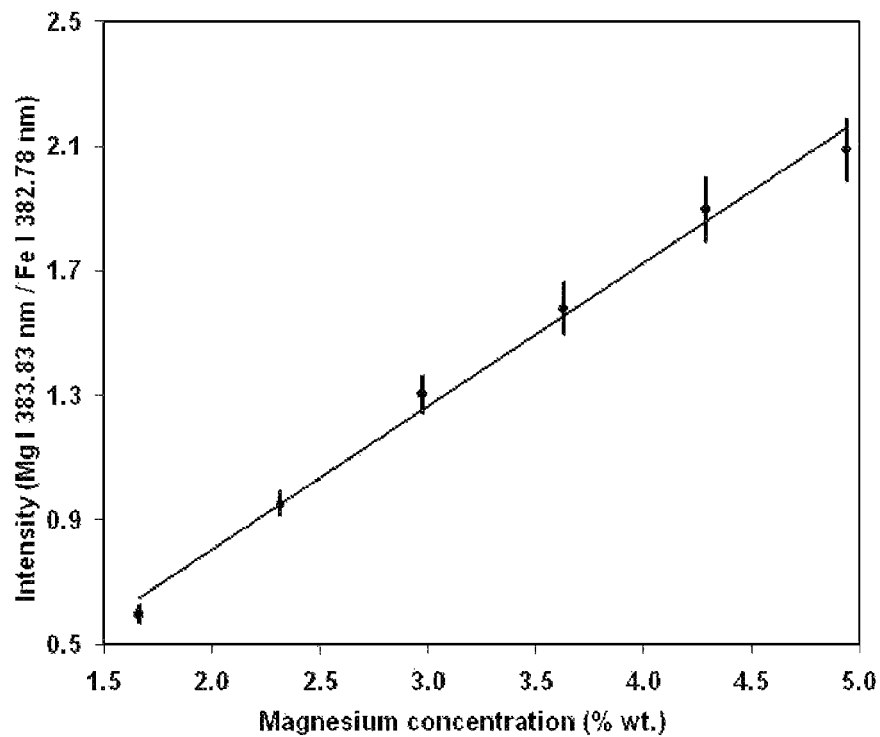
FIG. 9 is a calibration curve for magnesium in nickel ore slurry using the saturating 382.58 nm line of iron as internal standard.
Figure 10:
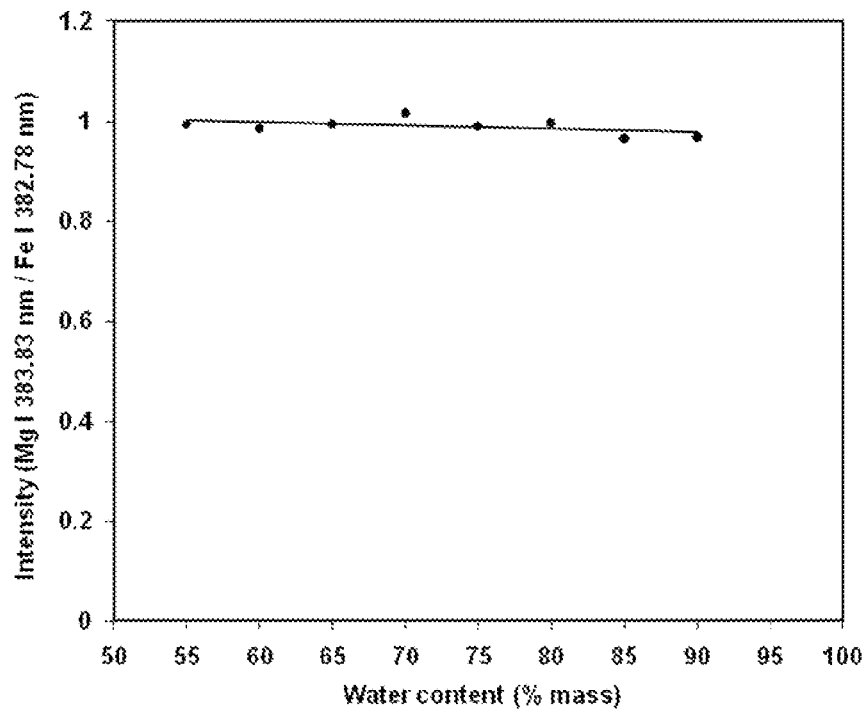
FIG. 10 shows variation of the magnesium/iron line intensity ratio versus the water content in the slurry.

For the analysis of Mg in this nickel ore slurry, the emission intensity at the center of the 383.83 nm line of Mg (i.e. the peak intensity) was divided by the intensity at center of the iron saturating line at 382.58 nm to yield the linear calibration curve shown in FIG. 9. This calibration is observed to be quite robust. In particular, the calibration curve is independent of the water content in the slurry as shown in FIG. 10.

Figure 11:
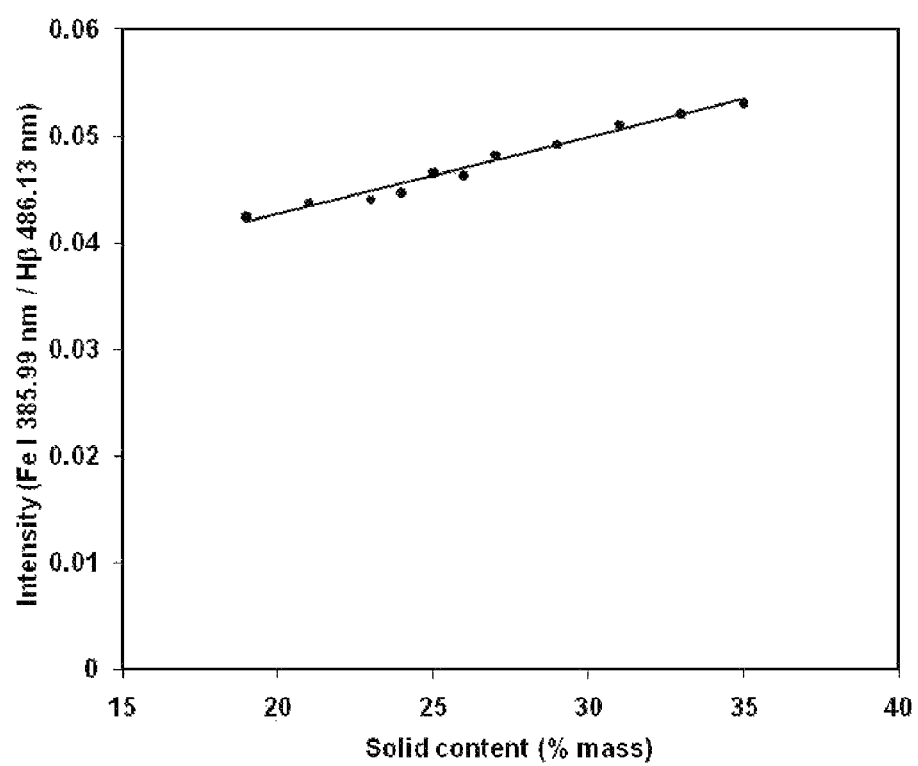
FIG. 11 is a calibration curve for the solid/liquid ratio using the ratio of a saturating iron line representative of the solid phase in the slurry to the Hβ hydrogen line representing the liquid phase.

It is also possible to use this approach to evaluate the quantity of water in the slurry. This is done by monitoring the peak intensity of the hydrogen Hβ line at 486.1 nm (shown in FIG. 8), which is solely associated to water since, in this case, there is no hydrogen in the solid ore, and using a saturating line associated with the solid. The linear calibration curve is shown in FIG. 11, in which the internal standard is another saturating line of iron at 385.99 nm.

In the case of the complex mixture of a nickel ore slurry indicated above, the calibration approach according to the invention is shown to work well. There are other cases in which, because of the very complex phenomena occurring in LIBS, an approach based on a single internal standard is not as effective. In such a case, calibration could be based on an ensemble of saturating lines of several elements and a matrix relating the concentration of these elements to lines or whole spectrum attributes (peak intensities or integrated intensities). Thus multivariate calibration can be performed as opposed to the univariate calibration which is based on a single ratio of a single internal standard to a single analyte line. See for example: *Laser-Induced Breakdown Spectroscopy of Steel: A Comparison of Univariate and Multivariate Calibration Methods*, in Applied Spectroscopy, vol. 64, pages 154-160, 2010, by C. B. Stipe, B. D. Hensley, J. L. Boersema and S. G. Buckley. Calibration may be established through a set of samples with composition variations between elements adequately chosen so that a robust correspondence matrix between concentrations of elements and spectral lines attributes can be established. Chemometric methods such as partial least squares and/or principal component analysis are often used to derive an efficient and robust calibration matrix. It is known in the art of multivariate calibrations, to build a calibration matrix based on as-recorded spectra using peak intensities or integrated intensities of lines. As an extension of the present examples, based on a saturating line of a minor element in the complex mixture, we found that there is a benefit to pre-process the various line attributes by normalizing them to the peak intensity(ies) of the saturating line(s) of an element. Applicant has verified that in these cases, the error of composition prediction was less with normalization to peak intensity of a saturating line than using raw line attributes.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A laser induced breakdown spectroscopy (LIBS) method, comprising:
   providing one or more reference samples, each having a respective, known concentration of an analyte;
   assaying each reference sample to obtain a respective LIBS spectrum; for each reference LIBS spectrum,
   measuring an intensity of at least one spectral analyte line that varies with concentration of the analyte, and
   measuring a peak amplitude of at least one saturating line of a reference element; and
   computing a ratio of the intensity to the amplitude as a function of the known concentration of the analyte, to produce a calibration curve for the analyte.

2. The method of claim 1 wherein measuring the peak amplitude is provided by an integrated intensity within a spectral band narrower than 1h a bandwidth of the saturating line that includes the peak of the saturating line.

3. The method of claim 1 wherein the measure of the amplitude of the saturating line is provided by a signal from a single narrow bandpass optical filter associated with a spectral feature of the line.

4. The method of claim 1 wherein computing the ratio as a function of the concentration comprises performing a linear regression.

5. The method of claim 1 wherein two or more saturating lines or two or more analyte lines are measured concurrently to improve calibration accuracy.

6. The method of claim 1 wherein providing the reference samples comprises applying chemometric methods to measure the concentrations in the reference samples.

7. The method of claim 1 wherein one or more of the at least one saturating line is used for normalizing intensities of at least one analyte line for each of a plurality of analytes.

8. The method of claim 1 further comprising:
   providing a test sample; assaying the test sample to obtain a test LI BS spectrum;
   measuring a test intensity of the test LIBS spectrum at one or more of the at least one spectral analyte line;
   measuring a test peak amplitude of the test LIBS spectrum at one or more of the at least one saturating line; and
   interpolating a concentration of the analyte in the test sample from a ratio of the test intensity to the test peak amplitude.

9. The method of claim 1 wherein the samples are complex mixtures.

10. The method of claim 1 wherein the samples are a solid, a liquid, a gas or a mixture thereof.

11. The method of claim 1 wherein the samples are slurries, aerosols, emulsions, or bubbles.

* * * * *